United States Patent [19]

Tu et al.

[11] Patent Number: 4,963,679
[45] Date of Patent: Oct. 16, 1990

[54] PROCESS FOR PREPARING BIS (3,5-DIOXOPIPERAZINYL) ALKANES OR ALKENES

[75] Inventors: Chin-Yun J. Tu; George W. Clark, both of Columbus, Ohio; Giampietro Borsotti, Novara, Italy

[73] Assignee: Erbamont, Inc., Dublin, Ohio

[21] Appl. No.: 157,195

[22] Filed: Feb. 17, 1988

[51] Int. Cl.$^5$ .......................................... C07D 241/18
[52] U.S. Cl. .................................................. 544/357
[58] Field of Search ..................... 558/346; 546/205; 71/103; 544/357

[56] References Cited

U.S. PATENT DOCUMENTS

| | | | |
|---|---|---|---|
| 2,461,519 | 2/1949 | Bersworth | 260/534 |
| 3,882,124 | 5/1975 | Kirchlechner et al. | 546/205 |
| 3,941,790 | 3/1976 | Creighton | 260/268 |
| 4,275,063 | 6/1981 | Creighton | 424/250 |
| 4,704,465 | 11/1987 | Lannert et al. | 558/346 |

FOREIGN PATENT DOCUMENTS 978724  12/1964  United Kingdom .

OTHER PUBLICATIONS

March, Advanced Organic Chemistry, (1986), p. 660 and p. 710.
Synthesis of $^{14}$C-Labeled Antitumor Agents, Il Synthesis of the Ring- and Side-Chain- $^{14}$C-Labeled DL-4,-4'-Propylenedi-2,6-Piperazinediones, Ying-Tsung Lin, et al.
The Preparation of 1,2-Propylenediaminetetra-Acetic Acid and its Resolution Through the Cobalt (III) Complex, Francis P. Dwyer et al., Dec. 17, 1958.

Primary Examiner—Mark L. Bell
Assistant Examiner—David M. Brunsman
Attorney, Agent, or Firm—Thompson, Hine and Flory

[57] ABSTRACT

A process for preparing a compound of the formula (I)

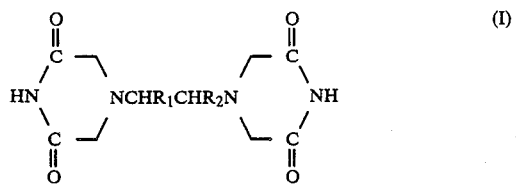

wherein $R_1$ and $R_2$ are individually selected from the group consisting of hydrogen and methyl or $R_1$ and $R_2$ together represent an ethylene bridge group comprising:
reacting a diamine of the formula (II)

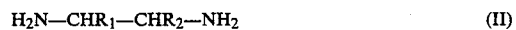

where $R_1$ and $R_2$ are defined as above with formaldehyde and an alkaline metal cyanide at a pH in the range of about 0 to 2 to produce a tetranitrile of the formula (III):

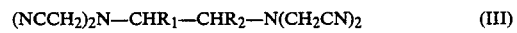

hydrating said tetranitrile to yield an acid addition salt of a tetraamide of the formula (IV):

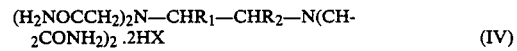

where $R_1$ and $R_2$ are defined as in formula (I) and X is an acid anion such as fluoride, chloride, bromide or sulfate but preferably chloride; and
reacting said acid addition salt of said tetraamide in a cyclization reaction to yield said compound of the formula (I).

10 Claims, No Drawings

PROCESS FOR PREPARING BIS (3,5-DIOXOPIPERAZINYL) ALKANES OR ALKENES

BACKGROUND OF THE INVENTION

The present invention relates to a novel process for preparing compounds of the formula (I)

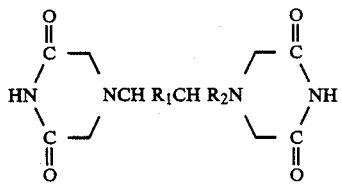

where $R_1$ and $R_2$ are individually selected from the group consisting of methyl and hydrogen or $R_1$ and $R_2$ in combination form an ethylene bridge. More particularly, the present invention relates to a novel process for forming the compounds (S)(+)-1,2-bis(3,5-dioxopiperazinyl)propane and (R)(−)-1,2-bis(3,5-dioxopiperazinyl)propane.

(S)(+)-1,2-bis(3,5-dioxopiperazinyl)propane is described in U.S. Pat. Nos. 3,941,790 and 4,275,063 to Creighton. It is known to display activity against tumors and other forms of cancer and to be useful as a synergist in combination with other anticancer agents. In particular, the compound has been found to exhibit activity with respect to sarcoma, lymphosarcoma and leukeima and to be particularly effective when used in a regimen in combination with Adriamycin.

Various methods for preparing compounds of the formula (I) are known in the art. The Creighton patents disclose two methods. In one (S)-1,2-diaminopropane is reacted with chloroacetic acid to form (S)-1,2-diaminopropane tetraacetic acid. The tetraacid is reacted with formamide under nitrogen at elevated temperature to yield the compound of formula (I). The second method consists of preparing the aforementioned tetraacetic acid as above, transforming it to the tetraamide by reaction with ammonia, and cyclizing the product British Pat. No. 978,724 describes another method for forming the tetraacetic acid in which diamines are reacted tetranitrile which is saponified. Bersworth et al. in U.S. Pat. No. 2,461,519 teaches a method for producing 1,2-diaminopropane tetracarboxylic acid by reacting 1,2-diaminopropane with formaldehyde and sodium cyanide at an alkaline pH.

These methods have not been satisfactory. In the first method of Creighton, the reaction of the diamine with chloroacetic acid requires a long period of time and separation of the tetraacid is difficult. Yields are relatively low. The second method of Creighton is also limited in terms of yield. Lin, Y.T. et al. *Radiopharm.* 1976 12(4) 592 attempted to form the tetraacid of 1,2-propane diamine using formaldehyde and sodium cyanide without success.

SUMMARY OF THE INVENTION

The present invention relates to a novel method for the preparation of compounds of the formula (I) in three steps which provides higher yields and shorter reaction times than known methods. In addition, isolation of intermediates is not required.

More particularly, the present invention relates to the preparation of (S)(+)-1,2-bis(3,5-dioxopiperazinyl)propane and (R)(−)-1,2-bis(3,5-dioxopiperazinyl)propane.

The method of the present invention comprises reacting a diamine of the formula (II):

where $R_1$ and $R_2$ are defined as above with formaldehyde and an alkaline metal cyanide at a pH in the range of about 0 to 2 to produce a tetranitrile of the formula (III):

hydrating said tetranitrile to yield an acid addition salt of a tetraamide of the formula (IV):

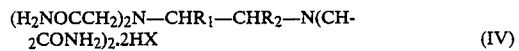

where $R_1$ and $R_2$ are defined as in formula (I) and X is an acid anion such as fluoride, chloride, bromide or sulfate but preferably chloride; and reacting said acid addition salt of said tetraamide in a cyclization reaction to yield said compound of the formula (I).

DETAILED DESCRIPTION

In accordance with the present invention, a solution of an amine of the formula (II) or an acid addition salt thereof (e.g., a hydrochloride, hydrobromide, tartrate, etc.) in water is prepared and mixed with a solution of formaldehyde and an acid such as sulfuric acid to adjust pH. It has been found that the pH of the nitrilation reaction is critical. It should be about 0 to 2. If the pH is higher, yield is poor. To this mixture a solution of sodium cyanide or another alkaline metal cyanide such as potassium cyanide is slowly added while maintaining the pH in the range of 0 to 2.

The formaldehyde is generally reacted in a stoichiometric excess. For example, about 4.25 mols of formaldehyde may be reacted for each mol of diamine. The concentrations of the reactants are not critical. The reaction is preferably carried out at a temperature of about 35° to 40° C. for the best yields. Depending upon reaction conditions, including concentration and the yield desired, the reaction may require several hours to complete The tetranitrile is readily recovered by extraction with methylene dichloride.

Conversion of the tetranitrile to the corresponding tetraamide is easily accomplished by dropwise adding a solution of the tetranitrile, for example, in methylene dichloride, to a solution of an acid. Suitable acids include mineral acids such as HCL, HBr, HF and $H_2SO_4$ at concentrations ranging from about 30 to 90%. The acid solution is preferably cooled to 0° C. before initiating the addition of the tetranitrile. After the addition of the nitrile is completed, the temperature is allowed gradually to rise to 20° C. A non-solvent such as acetone or ethanol is then added to force the tetraamide to precipitate from the solution.

It has been found that if the water is not removed from the tetraamide, it reduces the yield of the target compound particularly when the cyclization reaction is run at lower temperatures (e.g., 140°–145° C.). One means for removing water and improving yield is through the addition of thionyl chloride in an inert solvent such as methylene chloride. The resulting suspension can be subjected to the cyclization reaction directly. A less satisfactory approach to removing water from the tetraamide consists of adding 99% ethanol to the tetraamide and eliminating water by azeotropic distillation. The thionyl chloride procedure is illustrated in Example 4.

The acid addition salt of the tetraamide is preferably heated in melted phenol to about 140° to 170° C. to bring about cyclization of the piperazinyl rings. It has been found that reacting the acid addition salt of the tetraamide instead of the free base is particularly advantageous because it improves yield and reduces the temperature required for the reaction. The preferred acid addition salt is the hydrochloride. Upon heating this salt, the chloride reacts with ammonia liberated upon ring closure to produce ammonium chloride shifting the reaction equilibrium to favor formation of the piperazinyl compound.

Melted phenol is the preferred solvent for the cyclization reaction because the tetraamide salt is very soluble in the phenol and the phenol is sufficiently acidic to catalyze the reaction. The phenol also has a high boiling point. Other solvents having this combination of characteristics could also be used.

The invention is illustrated in more detail by the following non-limiting examples.

EXAMPLE 1

Preparation of
(S)-1,2-propylenedinitrolotetraacetonitrile

To a solution prepared by mixing 442 g of (S)-propandiamine.2HCl in 1800 ml water, 540 g of 96% sulfuric acid and 1200 ml formaldehyde (40%) in water, a solution of 795 g NaCN in 1800 ml water is slowly added over a period of four hours. The reaction is slightly exothermic and temperature is maintained at 34°–36° C. with external cooling. After two-thirds of the cyanide solution is added, the tetranitrile begins to separate as an oil. At the end of the addition, the reaction mass is heated for an additional 5 hours at 37°–39° C. After cooling to 25° C., the tetranitrile is extracted with several portions of $CH_2Cl_2$. The combined extracts are washed with 1N HCl in order to remove a coloured impurity and the solvent is evaporated under vacuum to give 625 g of the tetranitrile as a viscous yellow oil. The yield is 90% on the (S)-propandiamine.2HCl; $[\alpha]_D^{25} = 31.6°$ (c=1; $CH_2Cl_2$).

EXAMPLE 2

Preparation of
(S)-N,N,N',N'-Tetracarboxamidomethyl-1,2-diaminopropane dihydrochloride A solution of 300 g of the tetranitrile in 1 liter $CH_2Cl_2$ obtained in example 1 is added dropwise over a period of 12 hours to 1200 ml of HCl (37% in water) and cooled to 0° C. by external cooling. The temperature of the solution is subsequently allowed to increase to 20° C. over 3 hours. The reaction mass is stirred overnight at 20° C. A colourless organic layer is separated. The aqueous layer is added dropwise to 4 liters of well stirred acetone. A precipitate forms and is filtered and thoroughly washed with acetone. This can be used for the subsequent step or optionally dried at 50° C. under vacuum, to give 485 g of the title compound as a slightly yellow solid.

EXAMPLE 3

Preparation of S-1,2-bis(3,5-dioxopiperazin-1-yl)propane

To 2500 g of phenol warmed on an oil bath at 90° C. under a slow flow of Argon, 2000 g of the product in acetone obtained in Example 3 (dry content 565 g) is added over a period of 20 minutes. The temperature is gradually increased over 1.5 hours to 160° C. while the acetone is removed by distillation. After heating at 160°–170° C. for 1 hour, the oil bath is removed and the reaction mass is cooled to 120°–130° C. The $NH_4Cl$ that forms is filtered and the phenol solution is diluted with 3 liters of ethyl alcohol. On cooling to 15° C., a crystalline product separates, and is filtered, washed with ethanol and dried to give 244 g of white product (60% yield calculated using tetranitrile from Example 1 as starting material) m.p. 189°–91° C. Recrystallization from dioxane gives the target compound m.p: 191°–192° ,$[\alpha]_D^{20} = +40°$ (C=0.5 buffer solution at pH 6.7).

EXAMPLE 4

Modified Preparation of
S-bis(3,5-dioxopiperazin-1-yl)propane

A sampling of tetraamide (55% of free tetraamide with water content of 9.5%) obtained in Example 2 (50g) is stirred with 100 ml methylene chloride containing 18.5 ml thionyl chloride at 30°–35° C. for 45 minutes and added to 200 g of melted phenol. The mixture is heated to 140° C. and is kept at 140° C. for 2 hours as the methylene chloride is evaporated. Heating is continued for 6 hours at 140° C. 21.5g crude product (87% yield based on the tetraamide) is obtained. In a parallel experiment without the thionyl chloride/methylene chloride treatment, 71% yield is obtained at 165° C. and 62% yield is obtained at 140° C.

EXAMPLE 5

Preparation of (S)-1,2-Diaminopropane
bis(D-bitartrate)

Charge approximately 300 kg of water and approximately 180 kg of D(−) tartaric acid in a 760 L glass-lined vessel. Stir the mixture and rapidly add approximately 58 kg of DL-1,2-diaminopropane. (The reaction is exothermic and the temperature will rise to approximately 65° C.). Continue stirring and heat the mixture to 80°–85° C. until it becomes homogeneous. Cool slowly over approximately 16 hours to about 5° C. The (S)-1,2-diaminopropane bis(D-bitartrate) crystallizes out. Centrifuge the slurry and discard the mother liquor. Return the solids to the 760 L glass-lined reactor.

Charge approximately 300 kg of water into the 760 L glass-lined reactor and stir and heat the mixture to 80°–85° C. until (S)-1,2-diaminopropane bis(D-bitartrate) is completely dissolved. Cool the solution slowly over approximately 16 hours to about 5° C. Centrifuge the slurry to separate the crystallized (S)-1,2-diaminopropane bis(D-bitartrate). Discard the mother liquor and dry the solid (S)-1,2-diaminopropane bis(D-bitartrate) in a vacuum tray-drier at approximately 60° C. (Yield about 140 kg, 95%).

EXAMPLE 6

Preparation of (S)-1,2-Diaminopropane dihydrochloride

Charge a 760 L glass-lined reactor with approximately 700 L of methanol and approximately 140 kg of (S)-1,2-diaminopropane bis(D-bitartrate). Stir the mixture and then quickly add approximately 69 kg of hydrogen chloride gas. (The reaction temperature will increase to about 60° C. and mixture will become homogeneous). Continue stirring and slowly allow to cool to approximately 20° C. The (S)-1,2-diaminopropane dihydrochloride will begin to crystallize. Stir the reaction mixture at about 20° C. for 2-16 hours. Remove the solids by centrifugation. Wash the solids with methanol and then dry in a vacuum tray-drier at approximately 60° C. (Yield about 26 kg. 47%).

EXAMPLE 7

Preparation of (S)-1,2-propylenedinitrolotetraacetonitrile

Charge 40 kg of demineralized water into a 200 L glass vessel. Purge with nitrogen. Add slowly with stirring and external cooling, 12.2 kg of sulfuric acid (96%). Cool the solution to 25° C. and then add 10 kg of (S)-1,2-diaminopropane dihydrochloride and 26.1 kg of formaldehyde solution (40%). Then slowly add over a four hour period, a solution of 18 kg of sodium cyanide in 40 L of demineralized water. Keep the reaction temperature at 35°-40° C. The tetranitrile begins to separate as an oil after about two thirds of the cyanide has been added. Continue heating the mixture for approximately 5 to 8 hours until TLC analysis shows only one spot due to the presence of the tetranitrile.

Add 10 kg of demineralized water and cool to 25° C. Extract the oily tetranitrile with 3 portions of methylene chloride (36 kg then 18 kg and 18 kg, respectively). Combine the extracts and pour into a 100 L glass vessel and wash with five 10 kg portions of dilute hydrochloric acid (4%) and then six portions (15 L each) of demineralized water. Check the organic layer by TLC to ensure absence of any starting material or impurity having an Rf less than that of the tetranitrile (Rf 0.5). The weight of the organic solution is about 79 kg. A small portion of the solution is evaporated to dryness under vacuum and the residue weighed. Using this weight, the tetranitrile content of the whole solution is estimated (about 14 kg). (Yield about 90%)

EXAMPLE 8

Preparation of (S)-N,N,N',N'-Tetracarboxamidomethyl-1,2-diaminopropane dihydrochloride In a 200 L glass vessel charge approximately 34 kg of hydrochloric acid (37%) and externally cool to 0°-2° C. with acetone/dry ice.

Over a 3 hour period, keeping the temperature between 1 and 3° C., and stirring the mixture very well, add through a Teflon tube, approximately 39.5 kg of the methylene chloride solution of the tetranitrile prepared from Example 7. After the addition is complete, allow the temperature to slowly rise over a 3 hour period to room temperature. Stir overnight (12-16 h) at room temperature. Check by TLC for disappearance of tetranitrile and the formation of the tetraamide. Discard the lower colorless organic layer.

Place 72 kg of absolute ethanol into a 200 L glass vessel and stir. Over a 1 hour period pump the acidic solution through a Teflon tube into the ethanol. Cool the stirred mixture with an ice-water bath to keep the temperature between 16°-18° C. Stir for about one more hour and then centrifuge the resulting slurry. The solid is washed in the centrifuge with four portions of 12.5 L of absolute ethanol. The wet solid is dried in a vacuum oven at 35° C. and 30-35 mm Hg for about 24 hours. Yield about 11.6 kg of tetraamide (65-80%).

EXAMPLE 9

Preparation of (S)(+)-1,2-bis(3,5-dioxopiperazinyl)propane

Charge 8 kg of phenol in a 10 L glass vessel. Purge with nitrogen and heat to 90° C. Stir and add 2.3 kg (on dried basis) of the tetraamide prepared from Example 8. Over a 1 hour period raise the temperature to 145°-170° C. and maintain the temperature above 140° C. for 4 hours. At appropriate intervals withdraw a sample and examine by TLC for disappearance of tetraamide.

When the reaction is complete, cool the reaction mixture to 100° C. and rapidly filter the precipitated ammonium chloride, collecting the filtrate in a 25 L glass vessel. Wash the ammonium chloride precipitate with 3 L of ethanol. Dilute the hot phenolic solution with 10 L of ethanol. Externally cool using brine to about 20° C. with stirring over 2-4 hour period and for a further 12 hours cool to about 15° C. using water.

Filter the precipitated crude product and wash four times with 2 L of ethanol. Then slurry with 2 L of ethanol and finally wash with another 2 L of ethanol. Check for the absence of phenol by TLC. Dry for 18-24 hours at 40° C. under vacuum. The yield is about 900 g crude (S)(+)-1,2-bis(3,5-dioxopiperazinyl)propane.

(54-61%).

The product was purified as follows:

In a 20-L glass vessel, charge 9.0 L of pyrogen-free water or 4.5 L of pyrogen-free water and 4.5 L of ethanol and heat to 85°-95° C. Add about 900 g of crude product and stir rapidly until dissolution is complete (maximum time about 5 minutes). Filter the hot solution through layers of dicalite and decolorizing charcoal and collect the filtrate in a 20-L glass vessel. Cool rapidly to 5° to 10° C. using brine and keep at this temperature for about 1 hour.

Filter the crystalline product and wash in succession with approximately 0.8 L of pre-cooled (5° to 10° C.) pyrogen-free water then approximately 1.2 L of pre-cooled (5° to 10° C.) diethyl ether. Dry the product for at least 12 hours at 40° C. under vacuum. Withdraw a sample and place in an air-tight amber glass container. The yield is about 800 g (76-85% purified).

While the invention has been illustrated with respect to the preparation of (S)(+)-1,2-bis(3,5-dioxopiperazinyl)propane, it will be apparent that other compounds within the scope of formula (I) and, more particularly, (R)(-)-1,2-bis(3,5-dioxopiperazinyl)propane can be prepared by analogous processes.

Having described the invention in detail and by reference to preferred embodiments thereof, it will be apparent that modifications and variations are possible without departing from the scope of the invention defined in the appended claims.

What is claimed is:

1. A process for preparing a compound of the formula (I)

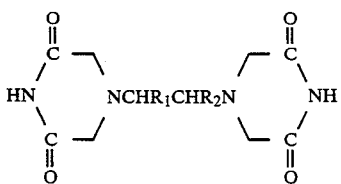

wherein $R_1$ and $R_2$ are individually selected from the group consisting of hydrogen and methyl or $R_1$ and $R_2$ together represent an ethylene bridge group comprising:

reacting a diamine of the formula (II)

$$H_2N-CHR_1-CHR_2-NH_2 \quad (II)$$

where $R_1$ and $R_2$ are defined as above with formaldehyde and an alkaline metal cyanide at a pH in the range of about 0 to 2 to produce a tetranitrile of the formula (III):

$$(NCCH_2)_2N-CHR_1-CHR_2-N(CH_2CN)_2 \quad (III)$$

hydrating said tetranitrile to yield an acid addition salt of a tetraamide of the formula (IV):

$$(H_2NOCCH_2)_2N-CHR_1-CHR_2-N(CH_2CONH_2)_2 \cdot 2HX \quad (IV)$$

where $R_1$ and $R_2$ are defined as in formula (I) and X is an acid anion selected from the group consisting of fluoride, chloride, bromide and sulfate; and reacting said acid addition salt of said tetraamide in a cyclization reaction to yield said compound of the formula (I).

2. The process of claim 1 wherein said cyclization reaction consists essentially of heating a solution of said acid addition salt of said tetraamide in a melted phenol.

3. The process of claim 2 wherein said alkaline metal cyanide is sodium cyanide.

4. The process of claim 3 wherein $R_1$ is methyl and $R_2$ is hydrogen.

5. The process of claim 4 wherein said diamine of the formula (II) is (S)-1,2-diaminopropane and said compound of the formula (I) is (S)-(+)-1,2-bis(3,5-dioxopiperazin-1-yl)propane.

6. The process of claim 1 wherein said acid addition salt of said tetraamide is mixed with thionyl chloride and methylene chloride prior to said cyclization reaction to remove water.

7. The process of claim 5 wherein said step of reacting said diamine is carried out at a temperature of about 35° to 40° C.

8. The process of claim 2 wherein said tetraamide is heated to about 140° to 170° C.

9. The process of claim 8 wherein X in the formula (IV) is chloride.

10. The process of claim 4 wherein said diamine of the formula (II) is (R)-1,2-diaminopropane and said compound of formula (I) is (R)-(−)-1,2-bis(3,5-dioxopiperazin-1-yl)propane.

* * * * *